(12) United States Patent
Pacak et al.

(10) Patent No.: US 9,681,887 B2
(45) Date of Patent: Jun. 20, 2017

(54) TROCAR SUPPORT

(75) Inventors: John Stephen Pacak, Winnipeg (CA); Heather Dawn Diamond, Winnipeg (CA); Caroline Alison Corbett, Winnipeg (CA)

(73) Assignee: Surgical Stabilization Technologies Inc., Winnipeg, MB (CA)

( * ) Notice: Subject to any disclaimer, the term of this patent is extended or adjusted under 35 U.S.C. 154(b) by 490 days.

(21) Appl. No.: 14/239,006

(22) PCT Filed: Aug. 10, 2012

(86) PCT No.: PCT/CA2012/050546
§ 371 (c)(1),
(2), (4) Date: Apr. 10, 2014

(87) PCT Pub. No.: WO2013/023293
PCT Pub. Date: Feb. 21, 2013

(65) Prior Publication Data
US 2014/0257356 A1    Sep. 11, 2014

Related U.S. Application Data

(60) Provisional application No. 61/524,470, filed on Aug. 17, 2011.

(51) Int. Cl.
*A61B 17/34*    (2006.01)
*A61B 17/00*    (2006.01)

(52) U.S. Cl.
CPC .......... *A61B 17/34* (2013.01); *A61B 17/3417* (2013.01); *A61B 2017/00539* (2013.01);
(Continued)

(58) Field of Classification Search
CPC ...... A61B 17/3417; A61B 2017/00539; A61B 2017/3486; A61B 2017/3492;
(Continued)

(56) References Cited

U.S. PATENT DOCUMENTS 3,044,468 A    12/1958    Birtwell
3,253,594 A    5/1966    Matthews
(Continued)

FOREIGN PATENT DOCUMENTS

CA    2447100    5/2002
EP    2238924    3/2010
(Continued)

*Primary Examiner* — Eric Rosen
*Assistant Examiner* — George J Ulsh
(74) *Attorney, Agent, or Firm* — Adrian D. Battison; Ade & Company Inc.

(57) ABSTRACT

A support apparatus for supporting a trocar while the trocar extends through a body wall of a patient includes an inflatable collar extending around the trocar which can be inflated to a predetermined size by a source of fluid where the source of fluid is located on the trocar support apparatus itself so as to be carried thereby and is defined by a pump mechanism to provide a fixed volume allowing inflation only to a fixed size. An abutment member is shaped to be received on an outer surface of the trocar sleeve and adjustable longitudinally of the trocar sleeve so as to be located at a selected position. A tube connecting the pump on the abutment to the inflatable collar is wrapped helically around the sleeve of the trocar. The collar includes a sleeve portion which can be unrolled on to the trocar sleeve.

21 Claims, 6 Drawing Sheets

(52) U.S. Cl.
CPC .............. *A61B 2017/3486* (2013.01); *A61B 2017/3492* (2013.01)

(58) Field of Classification Search
CPC .......... A61B 17/34; A61B 2017/00637; A61B 2017/0237; A61B 2017/0243; A61B 2017/348; A61B 2017/3488; A61B 2017/349; A61B 18/1487; A61B 17/0218; A61B 17/00; A61B 17/3415; A61B 17/3421; A61B 17/3498; A61B 2017/00477; A61B 2017/00557; A61B 2017/3419; A61B 2017/347; A61B 17/3423; A61B 2017/22051; A61B 2017/3433; A61B 2017/3445; A61M 2039/0626; A61M 39/0247; A61M 39/06; A61M 25/04; A61M 2039/0261; A61M 2039/0273; A61M 2039/0279; A61M 2039/0294; A61M 2039/062; A61M 2039/0686; A61J 15/0053

USPC .......................................... 606/184; 248/49
See application file for complete search history.

(56) References Cited

U.S. PATENT DOCUMENTS

| | | |
|---|---|---|
| 4,861,334 A | 8/1989 | Nawaz |
| 5,147,316 A | 9/1992 | Castillenti |
| 7,597,688 B1 | 10/2009 | Masson |
| 7,998,113 B2 | 8/2011 | Swisher |
| 2007/0213675 A1 | 9/2007 | Albrecht et al. |
| 2007/0239108 A1 | 10/2007 | Albrecht et al. |
| 2009/0221960 A1 | 9/2009 | Albrecht et al. |
| 2010/0081994 A1 | 4/2010 | Zisow |
| 2010/0152664 A1 | 6/2010 | Davis et al. |

FOREIGN PATENT DOCUMENTS

| | | |
|---|---|---|
| WO | 03094994 | 11/2003 |
| WO | 2007109700 | 9/2007 |

TROCAR SUPPORT

This application claims the benefit under 35 USC 119 (e) of Provisional Application 61/524470 filed Aug. 17 2011.

This invention relates to an apparatus arranged to locate and hold a trocar in position through the wall of the body of the patient.

BACKGROUND OF THE INVENTION

Many prior art documents provide arrangements where a trocar (or other wall penetrating device) is held in place by an abutment on the exterior and an inflated balloon on the interior.

U.S. Pat. No. 3,253,594 issued 1966 to Matthews shows a crude arrangement of this type (called a peritoneal cannula) with a flat washer on the exterior forming an abutment which is held in place by a screw and an inflatable balloon on the interior. The balloon is inflated by a supply of saline from an external source through a lumen which is a simple tube which may or may not be circular in cross-section.

U.S. Pat. No. 4,861,334 issued 1989 to Nawaz shows a more effectively engineered of this type, called a gastrostomy tube, with a domed washer on the exterior held in place by a screw and an inflatable balloon on the interior. The balloon is inflated through a channel in the interior of the tube fed through an exterior port by a supply of air from an external source.

Many subsequent patents are cited as improvements to the arrangement of Nawaz.

In a number of published applications Applied Medical Resources (Albrecht et al) disclose that it is known to attach an inflatable collar to a trocar. For example:

US 2007/0239108 and US 2007/0213675 claim a sleeve as a cannula with a balloon, but are limited to the use of annular grooves and longitudinal channel, to provide the fluid communication from the inlet to the balloon;

US 2009/0221960 claims first and second inflatable sections or balloon and an inlet port. This document mentions that the retention device can be formed as a separate unit for attachment to an existing trocar. This is not a new idea. US 2010/0081994 of Zisow provides a hinged end section of the trocar sleeve which pivots to resist pull out of the trocar.

Telflex Medical and Applied Medical Resources both appear to have related products and an extensive number of previous patents but no additional patents or applications of relevance to this subject have been located.

All publications, patents, and patent applications mentioned in this specification are herein incorporated by reference to the same extent as if each individual publication, patent, or patent application was specifically and individually indicated to be incorporated by reference, or may be referred to for any further details of such devices.

SUMMARY OF THE INVENTION

It is one object of the invention to provide a trocar support which can be used with an existing trocar to assist in holding the trocar in place during medical procedures.

According to one aspect of the invention there is provided a trocar support apparatus for supporting a trocar while the trocar extends through a body wall of a patient, the support comprising:

at least one inflatable member extending around the trocar which can be inflated to a predetermined size by a source of fluid; wherein the source of fluid is located on the trocar support apparatus so as to be carried thereby.

According to a second aspect of the invention there is provided a trocar support apparatus for supporting a trocar while the trocar extends through a body wall of a patient, the support comprising: at least one inflatable member extending around the trocar which can be inflated to a predetermined size by a source of fluid;

wherein the source of fluid is a pump mechanism forming a part of the trocar support and operable by hand.

According to a third aspect of the invention there is provided a trocar support apparatus for supporting a trocar while the trocar extends through a body wall of a patient, the support comprising:

at least one inflatable member extending around the trocar which can be inflated to a predetermined size by a source of fluid;

wherein the source of fluid provides a fixed volume allowing inflation only to a fixed size.

Preferably the inflatable member comprises a collar surrounding the trocar.

In one arrangement the trocar support forms an integral structure with the trocar itself so that they are supplied and used as a common element. However, as trocars are widely available and of different types, it is often more suitable to provide the support as a separate element in the general form of a sleeve so that the trocar can be inserted into an mounted on the sleeve for insertion into the incision in the patient.

Preferably, therefore, the trocar support apparatus comprises a separate element arranged for attachment to a trocar and comprising an abutment member shaped to be received on an outer surface of the trocar sleeve, the abutment member being arranged so as to be adjustable longitudinally of the trocar sleeve so as to be located at a selected position, said at least one inflatable member being arranged for mounting on the trocar sleeve at a position spaced from the abutment member such that said at least one inflatable member while deflated can be inserted on the trocar sleeve through an incision in the body wall and can be inflated when inserted to engage an inside surface of the body wall and such that the abutment member can be moved to a position to hold the body wall between the abutment member and the said at least one inflatable member. However the trocar support apparatus may form an integral part of the trocar itself and be supplied as a composite construction.

In one arrangement, the source of fluid is carried on the abutment member. However it can also be carried on another component of the trocar support but as an integral item therewith so that the whole trocar support includes the necessary inflation device. This allows the inflation device to be properly and easily controlled to provide the required amount of inflation fluid.

Preferably therefore the source of fluid is a manually operable pump. However other one time shots of fluid can be provided as part of the device.

Preferably a tube connects the fluid source on the trocar support to the inflatable collar. The tube can be wrapped helically around the sleeve of the trocar so that its axial length along the trocar can be adjusted without stretching or affecting its operation.

Preferably the tube is of a circular cross-section, however, in some cases it could have a flattened cross-section so as to lie flat against the sleeve of the trocar to allow the trocar sleeve to be inserted though the incision without interference from the tube.

Preferably the inflatable collar includes a sleeve portion which can be unrolled on to the trocar sleeve to engage around the trocar sleeve along a length of the trocar to provide a resistance to slipping longitudinally along the trocar during insertion.

Preferably the inflatable collar and the abutment member form a common collar portion which can be engaged onto the trocar sleeve and moved axially therealong. Thus they commence as a common item to be applied onto the outside of the trocar sleeve and then separated as the deployment occurs.

Preferably there is provided a plastic rigid support collar for supporting the flaccid inflatable collar. The support collar is attached to the abutment member and moves therewith onto the trocar sleeve. The support collar is then removable from the abutment member and the inflatable collar when the inflatable collar reaches its required axial position.

Preferably the support collar includes a manually operable release member to release the support collar from the inflatable collar.

Preferably the support collar includes a rigid protective cover for engaging over a manually operable element of the source of fluid to prevent premature inflation.

Preferably there is provided a manually operable device on the support collar for operating on the inflatable collar at the required axial location to hold the inflatable collar against axial movement at the required location on the trocar sleeve.

Preferably the abutment member can move axially along the trocar sleeve from the inflatable collar when the latter has reached its required axial location with the tube being extended along the trocar sleeve as the abutment member moves away from the inflatable collar.

Preferably the abutment member comprises a collar with a manually operable clamp for engaging the trocar sleeve.

Preferably the source of fluid includes a manually operable member which can be depressed to drive the fluid to the inflatable collar.

Preferably there is provided a manually operable device for operating on the inflatable collar at the required axial location to hold the inflatable collar against axial movement at the required location on the trocar sleeve.

An arrangement can also be comprised of the above concept of providing the source of fluid or pump on the device itself so that the source provides a fixed volume allowing inflation only to a fixed size.

The preferred design integrates the hand operated pump mechanism into the upper abutment. However, as an alternative, the hand operated pump could be separate from the upper abutment, but still permanently connected to the lower inflatable collar and delivering a fixed volume of fluid. And as another alternative it could be attached to the abutment, but not necessarily integrated.

An arrangement can also be provided in which the hand operated pump is part of the system but not integral with the abutment. The key point is that for safety, convenience and accuracy it always provides the optimum volume of fluid required to fully inflate the balloon and it always fully deflates the balloon. Over-inflation could lead to a rupture of the balloon while it is inserted within the patient and extraction of a trocar, whereas if the balloon is unknowingly only partially deflated, it may result in significant injury to a patient. In addition, under-inflation may result in the trocar not being properly supported during the procedure. Furthermore, having a self contained fluid supply eliminates the need for an external fluid supply port, which could be confused with the existing Trocar external port. Medical staff might accidently connect to the wrong port which may compromise the device and the procedure. As well, having a self contained fluid source eliminates the additional steps of having to choose an external fluid source and connecting the external source. Finally, if an external fluid source is required there is a risk of selecting the wrong external source (either volume or fluid), which may compromise the device or procedure by over-inflation, under-inflation or by insufficient deflation.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

In FIGS. 1 to 9 is provided a trocar support 10 for attachment to a trocar 12 to support a sleeve 11 of the trocar 12 while the sleeve 11 penetrates through a body wall 13 of a patient.

Figure 4:
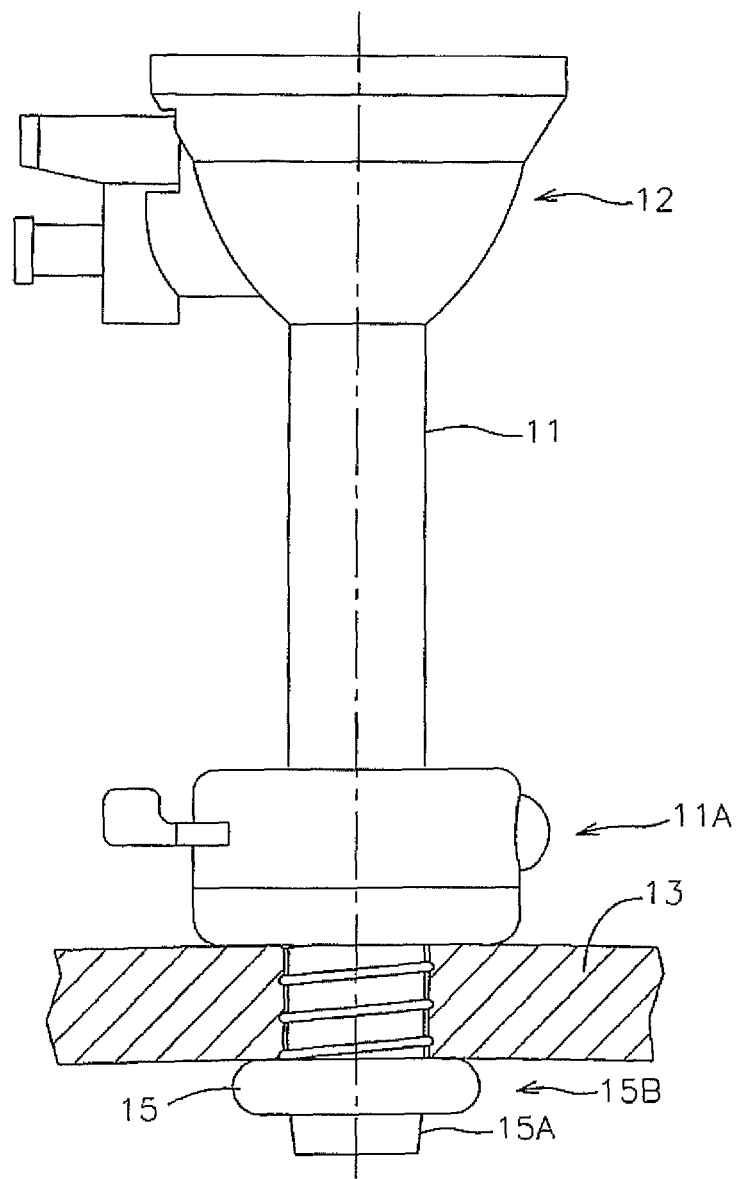
FIG. 4 is a side elevational view of the embodiment of FIG. 1 shown installed and in operation on a trocar.

The support 10 comprises an abutment member 14 shaped to be received on an outer surface of the trocar sleeve. The abutment member forms a collar 14A surrounding the sleeve with a manually operable over-center clamp 14B for releasable connection to the sleeve 11 so as to be adjustable longitudinally of the trocar sleeve 11 so as to be located at a selected position 11A as shown in FIG. 4. The support 10 includes an inflatable collar 15 for mounting on the trocar sleeve 11 at a required position 15B spaced from the abutment member 14 at the position 11A. The inflatable collar can be inflated by a source of fluid, typically air or other gas, from a pump 17 to a predetermined size through a supply tube 16.

Figure 9:
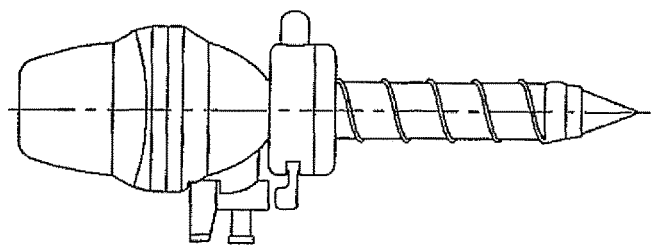
FIGS. 5 to 9 are side elevational views of the embodiment of FIG. 1 showing the steps of installation on to the trocar.

As shown in FIG. 9, the inflatable collar while deflated can be inserted on the trocar sleeve through an incision in the body wall and can be inflated from the pump 17 through the tube 16 when inserted to the inflated condition shown in FIG. 4 at 15B to engage an inside surface of the body wall 13. The abutment member can be moved to a position 11A to hold the body wall 13 between the abutment member 14 and the inflatable collar 15.

The source of fluid provided by the pump 17 is located on the trocar support and particularly the abutment member 14 so as to be carried thereby. The pump 17 includes a manually compressible button 17A which extends into a cylinder 17B to drive a measured volume of the fluid to the inflatable collar. The button 17A has a latch 17D which holds it compressed to keep the inflation until extraction is required whereupon the latch 17D can be released by a further press on the button 17A to allow a spring 17C to expel the button and extract the fluid from the collar 15.

The source of fluid therefore is a pump mechanism forming a part of the trocar support and operable by hand. The source of fluid 17 provides a fixed volume allowing inflation of the collar 15 only to a fixed size.

The tube 16 is of a circular cross-section or in some cases of a flattened cross-section so as to lie flat against the sleeve of the trocar and is wrapped helically around the sleeve of the trocar. Thus it can lie in compressed side by side turns as shown in the initial position in FIG. 1 and can extend axially as shown in FIG. 9.

The inflatable collar 15 includes a sleeve portion 15A extending downwardly from a bottom edge of the collar which can be unrolled on to the trocar sleeve as shown in FIG. 4. In the initial position shown in FIG. 1, the collar and sleeve are rolled up into the structure for later deployment.

Figure 1:
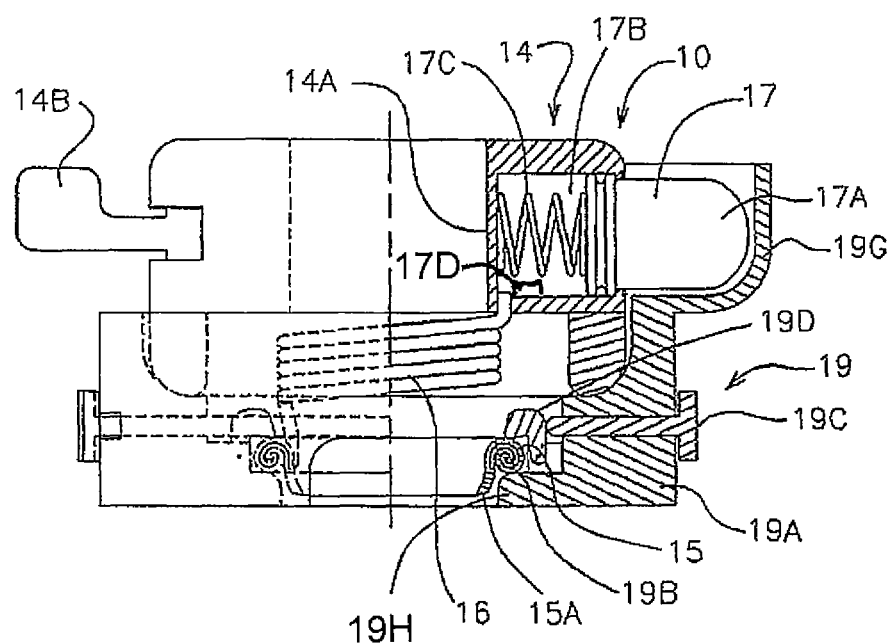
FIG. 1 is a side elevational view of a first embodiment of trocar support according to the present invention, the view being partly in cross-section.
Figure 2:
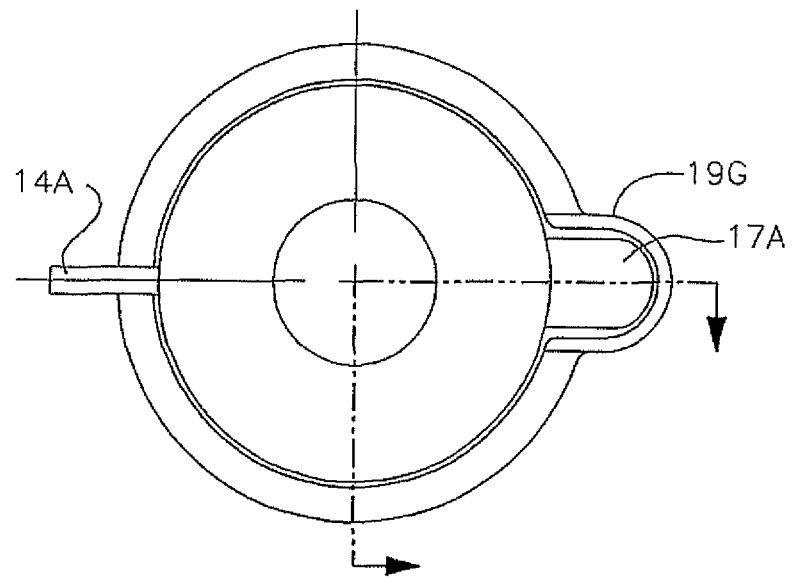
FIG. 2 is a top plan view of the embodiment of FIG. 1.
Figure 3:
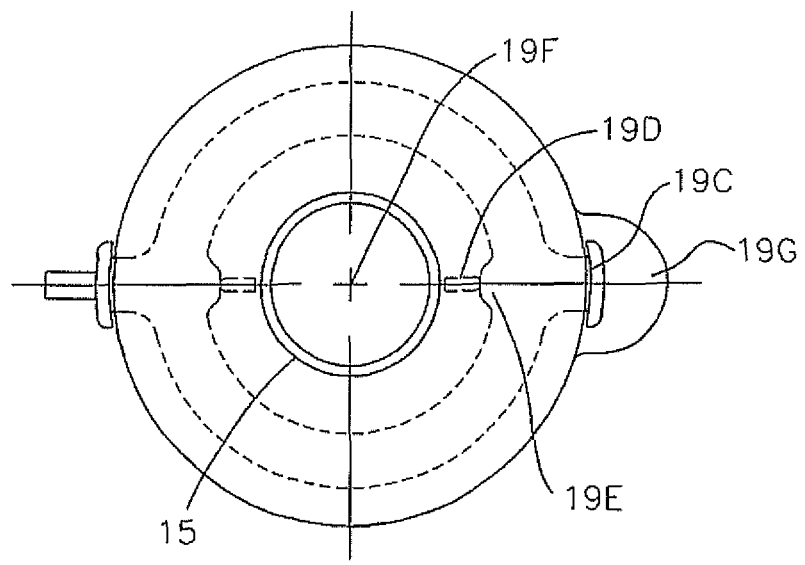
FIG. 3 is a bottom plan view of the embodiment of FIG. 1.
Figure 8:
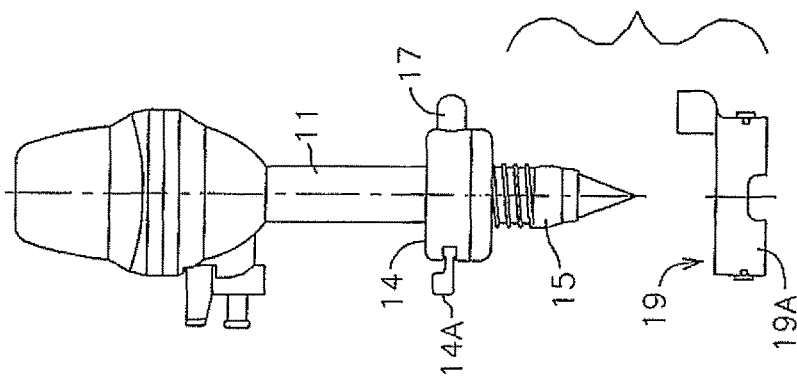
Figure 7:
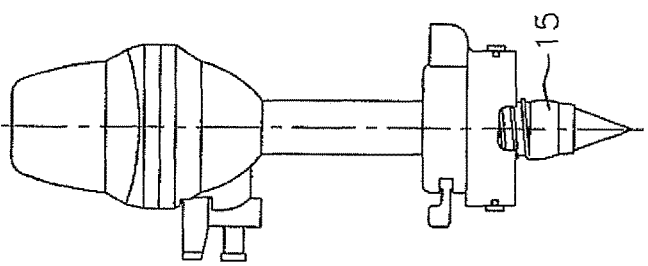
Figure 6:
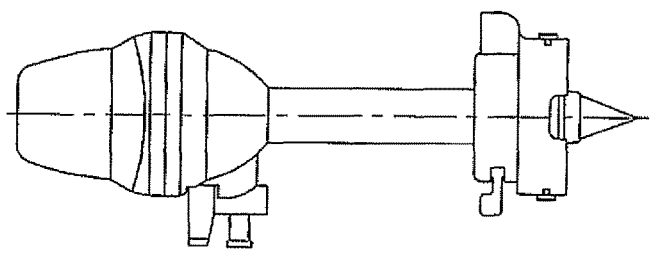
Figure 5:
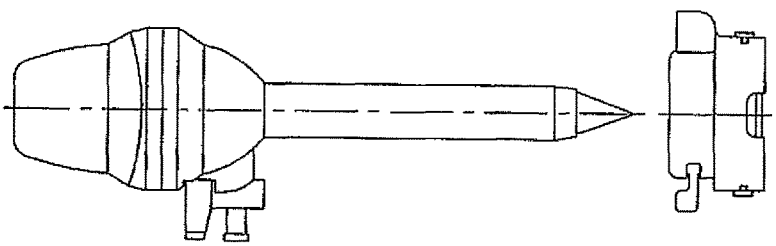

As shown in FIG. 1, the inflatable collar 15 and the abutment member 14 form a common collar portion which can be engaged onto the trocar sleeve 11 and moved axially therealong from the lower insertion end to a required position along the length of the trocar sleeve. In order to hold the assembly rigid and intact for insertion onto the trocar, there is provided a support collar 19 which surrounds the inflatable collar 15 which is attached to the abutment member 14 and moves therewith onto the trocar sleeve. The support collar includes a collar 19A with a hollow interior 19B forming a shelf 19H carrying the collar 15. This holds the collar in place, protects it, and helps maintain its sterility by eliminating the need to touch the inflatable collar while the device is moved into place. The support collar 19 is removable axially from the abutment member and the inflatable collar in a direction over the end of the trocar 11 when the inflatable collar 15 reaches its required axial position as shown in FIG. 8. The support collar 19 includes a manually operable release member 19C, 19D to release the support collar 10 from the inflatable collar 15. This operates by a lever 19D holding the collar 15 in place until release is required whereupon a manually operable member 19C is operated to release the lever and to allow the collar 15 to unroll and then the collar 19 to move axially away from the collar 15. As shown in FIG. 3, the member 19C can form a cam with lobes 19E which hold the lever 19D in place until the lobes are rotated around a longitudinal axis 19F releasing the levers and allowing the collar 15 to be deployed. Lever 19D can be loaded with a spring, which will ensure that the lever pivots away from the inflatable collar when released. As an alternative to the cam arrangement described above, member 19C' can be a manually operable push button, which holds lever 19D in place when pressed once and releases the lever when pressed again. When pressed, the button has a latch, which keeps it 30 compressed. The latch is released by a further press on the button to allow it to be expelled by a spring.

The support collar 19 is molded from a plastic material so as to be rigid to protect the inflatable collar and includes a protective cover 19G at one side forming a cup for engaging over the manually operable button 17A of the pump 17.

The abutment member 14 can move axially along the trocar sleeve from the inflatable collar 15 when the latter has reached its required axial location 15B with the tube 16 being extended along the trocar sleeve as the abutment member moves away from the inflatable collar.

Figure 10:
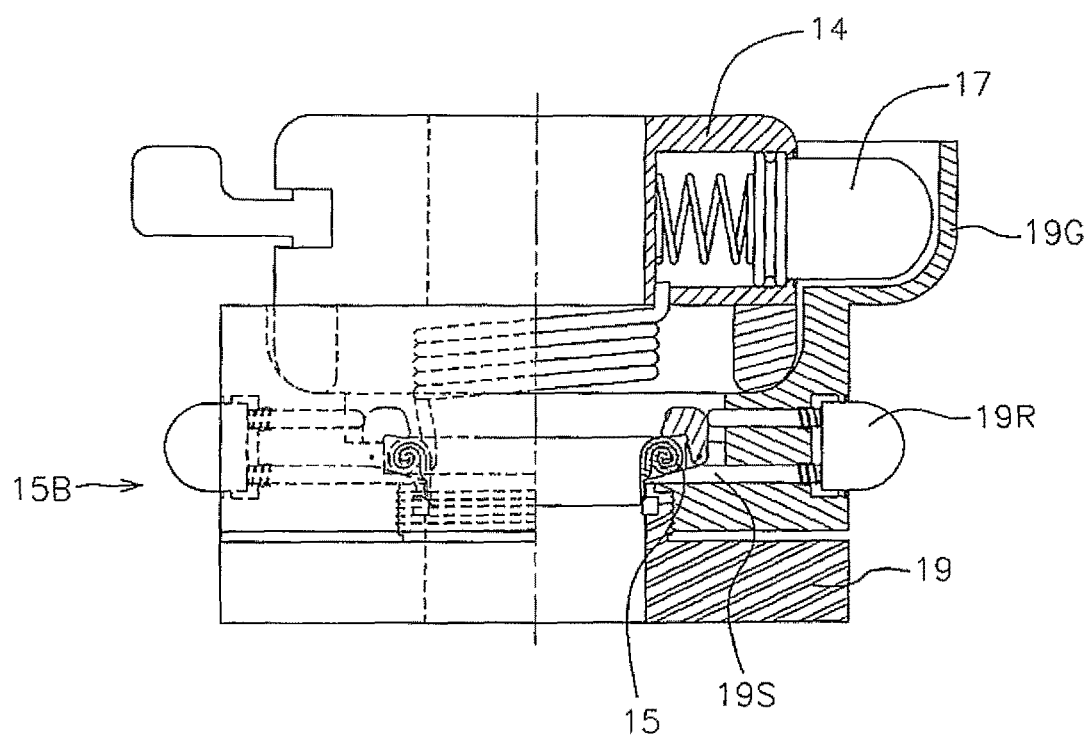
FIG. 10 is a side elevational view of a second embodiment of trocar support according to the present invention, the view being partly in cross-section.

As shown in FIG. 10 there is provided when required a manually operable device 19S on the support collar 19 operable by a button 19R for operating on the inflatable collar 15 at the required axial location 15B on the trocar to hold the inflatable collar 15 against axial movement at the required location 15B on the trocar sleeve. This device 19S can operate using many different techniques as described below, so as to ensure that the collar 15 remains at the required location until the inflation secures it more effectively.

Additional attention may be required in regard to some constructions to ensure that the lower inflatable collar remains in place after application of the device to the trocar and while the trocar is inserted into an incision in the body wall of the patient. Thus for example the following additional constructions can be used as the manually operable device 19S:

A portion of coiled metal spring material can be located embedded within or on the lower collar of the inflatable abutment. When the trocar is inserted, the spring is forced to expand causing the inflatable abutment to grip the wall of the trocar sheath.

A circular ferrule, coil or split ring can be swaged into position using swaging tool features built into the device support collar. A cam system is used to apply force to metal elements, which transfer that force to the outer diameter of the circular ferrule, coil or split ring causing it to plastically deform securing the inflatable abutment into position. Alternatively, a threaded compression fitting system built into the support collar, similar to what is shown in FIG. 10, can be used to swage the ferrule, coil or split ring into position. The threaded lower portion of the support collar is manually operable by rotating it relative to the threaded upper portion of the support collar causing them to close together and transfer force to outer diameter of the circular ferrule, coil or split ring causing it to plastically deform securing the inflatable abutment into position.

The device support collar can have an arrangement to hold a spring coil/split ring open until the trocar is inserted into position. The spring coil/split ring is then released applying the spring force to lower collar of the inflatable abutment securing it into position on the trocar sleeve.

The inner diameter of the elastic collar of the inflatable abutment can have an adhesive surface that is covered until ready for use. The removable device support collar has an arrangement to hold the inflatable collar stretched open. Once the adhesive is exposed and the trocar is inserted in position the inflatable collar is released.

The device support collar can have an arrangement to cinch an embedded fine wire or band attached to the lower collar of the inflatable abutment.

In addition, the arrangement described herein can be modified in a number of alternative arrangements and options which can be used as follows:

The fluid supply cylinder can be replaced by a fluid bladder which is compressed by a manually operable element;

Inflation of the balloon will help further secure the inflatable to the trocar sleeve as discussed;

The spiral fluid conduit surrounding the trocar sleeve can be formed as an oval or band to allow for an increased fluid flow rate while allowing for a smaller overall outer diameter while wrapped around the trocar;

The fluid conduit connecting the upper and lower abutments could be arranged vertically along the axis of the trocar with excess conduit allowed to remain unsecured as the upper abutments is moved towards the lower abutment.

Another option is for the upper abutment to have a mechanism for self retracting the excess fluid conduit as the upper abutment is moved towards the lower abutment.

Larger trocars require a larger inflatable portion and therefore require more fluid to fulfill inflation. To accommodate this there may be provided an additional fluid supply cylinder or bladder on the opposite site of the existing fluid supply, as required;

Another approach is to utilize a self-expanding supply bladder that wraps around part of the trocar (within the upper abutment) and has sufficient volume to fully inflate the lower portion when fully compressed. This is a closed system comprising the bladder, fluid conduit and the lower inflatable portion;

Another option is to use a manual multi-stroke pump with a bleed valve to prevent over-inflation and an indicator to show when the lower portion is fully inflated and fully deflated. The pump is then reversed for deflation;

Another option can be provided that still utilizes the fluid delivery system, but does not have a fluid conduit retraction system in the upper abutment. In this case, the upper fluid supply is in a fixed position at the proximal end of the trocar sleeve, but another collar, which translates along the axis of the trocar sleeve, becomes the upper abutment. The fluid conduit is fully extended all the time and is held in place along the outer surface of the trocar sleeve by a sheath.

The lever mechanism shown on the top of the upper abutment is used to secure the upper abutment in position on the trocar via a collar that tightens around the trocar. An alternative is to make this a push button feature for greater ease of use. The button is located on the circumference of the upper abutment in the same way that the inflation pump is shown. Depressing the button applies pressure on the wall of the trocar sleeve, thus, holding it in position.

The device can also be manually installed onto the trocar sleeve by hand without using the support collar. The trocar is inserted into the device and the inflatable collar is drawn along the axis of the trocar sleeve and unrolled onto the trocar sleeve by hand at the desired position.

Another trocar concept can be provided that is significantly different in form, but still utilizes a fixed volume fluid delivery system. The fluid delivery system is fixed in position at the proximal end of the trocar sleeve and inflates ribs or rings along the length of the trocar sleeve once it is in the desired position. The rings can also be comprised of solid elements which are pneumatically actuated to protrude from the wall of the trocar sleeve and withdrawn when the trocar sleeve is to be extracted. In another arrangement there can be control over which rings are inflated or actuated. There would be no upper or lower abutment.

It is also possible to get the inflatable abutment onto the trocar without requiring that it be rolled on. If that is the case, here are three design options to include:

a) The device support collar can have an arrangement to hold the leading edge of the unrolled inflatable abutment open until the trocar is inserted into position. The trocar is then pushed into the opening and forced through until it is in the desired location. Once in position the opening is released.

b) The device support collar has the means to hold the entire unrolled inflatable abutment open until the trocar is inserted into position. The inflatable abutment is then released securing it into position on the trocar sleeve.

c) A disposable tubular frame is used to hold the inflatable abutment open until the trocar is in position. Once in the desired position, the disposable frame is removed leaving the inflatable abutment on the outer diameter of the trocar sleeve. This is achieved with or without the assistance of the device support collar. If the support collar is used, the frame is engaged with the support collar. If the support collar is not utilized, the frame engages the device itself either at the base of the upper abutment or through channels contained within the inner diameter of the upper abutment.

Figures 11, 12:
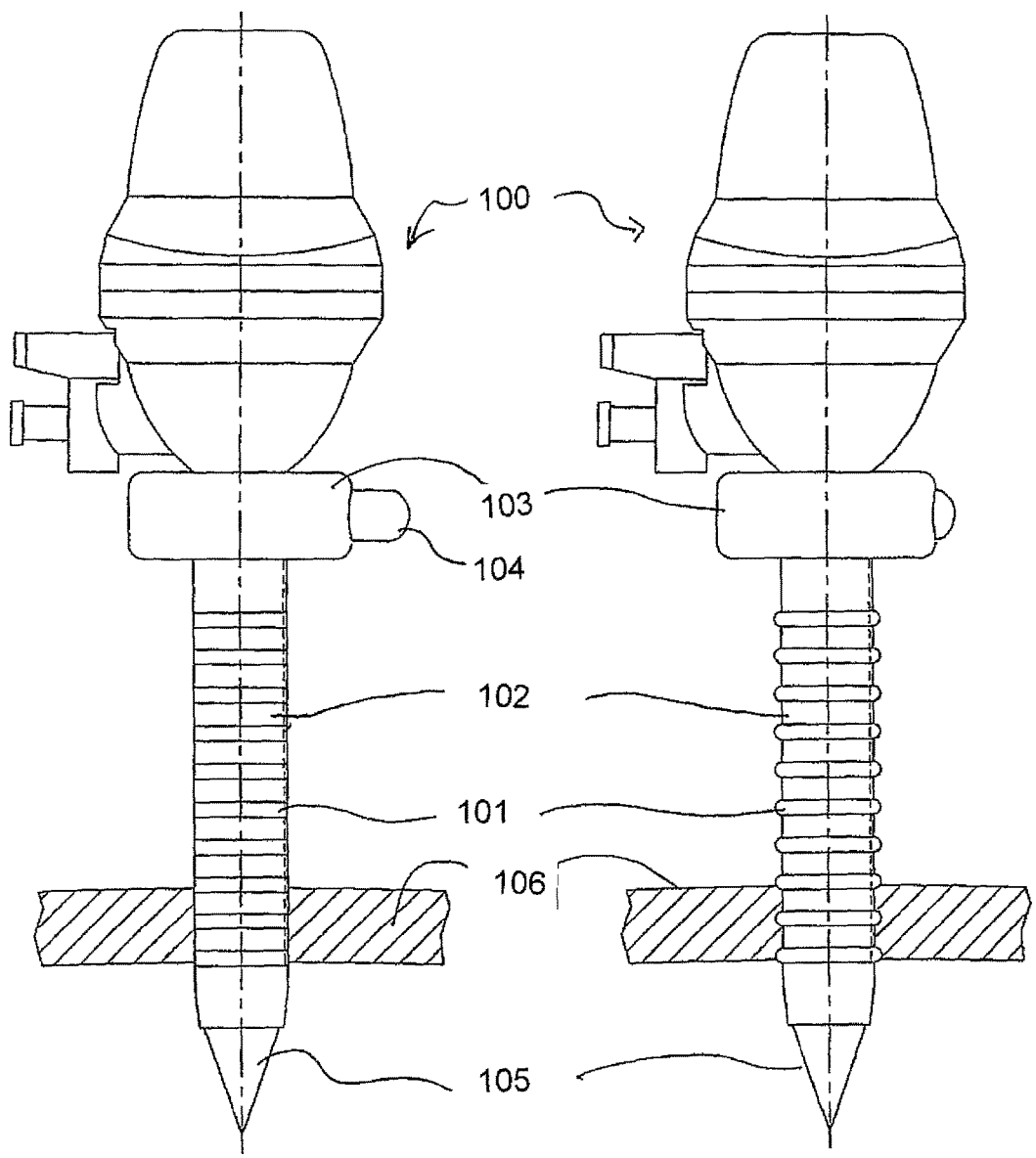
FIGS. 11 and 12 are side elevational views of a third embodiment of trocar support according to the present invention.

FIGS. 11 and 12 are side elevational views of a third embodiment of trocar support according to the present invention where the trocar support is an integral part of the trocar itself.

Also in this case, there is no separate inflatable collar but instead the trocar itself has a series of inflatable rings.

Thus FIGS. 11 and 12 show respectively the trocar 100 with a trocar shaft 102 having a tip 105 for insertion through the incision in the wall of the patient body 106. The trocar shaft has formed on the exterior wall a series of rings 101 which can be annular around the shaft or helical along the shaft and act to locate the trocar shaft in the incision. As previously described there is provided an abutment 103 at the end of the shaft to engage the exterior of the wall 106 where the abutment carries a hand pump 104 for inflating the rings 101. Thus as previously described, the source of fluid is located on the trocar support apparatus so as to be carried thereby, provides a pump mechanism forming a part of the trocar support and operable by hand and the source of fluid provides a fixed volume allowing inflation only to a fixed size.

This arrangement is more convenient for a surgeon to insert and remove from the patient than the conventional arrangements of this type where the protrusions are actually a course thread and the trocar sleeve must be threaded into and out of the incision and fascia. The twisting action while inserting or removing a conventional threaded trocar can traumatize the fascia. The described arrangement is intended to be engaged within the fascia itself after it is inserted, thus avoiding potential damage to the fascia from the twisting action.

In the present arrangement the inflation is effected by an inflatable manual pump of the type previous described which is carried on a collar part of the trocar itself. This controls the amount of fluid applied and obviates the need for separate fluid source.

The invention claimed is:

1. A trocar support apparatus for use with a trocar separate from the apparatus for maintaining the trocar in fixed position in a body wall of a patient while the trocar extends through the body wall of a patient, the support apparatus comprising:

an annular expandable member separate from the trocar and shaped and arranged to be received on and directly contact an outer surface of the trocar and movable along the trocar from a position separate from the trocar to a position located on the trocar, said annular expandable member being movable in an expansion movement from a collapsed condition radially outwardly of the trocar to a predetermined size;

an annular abutment collar separate from the trocar and shaped and arranged to be received on and directly contact an outer surface of the trocar and movable along the trocar from a position separate from the trocar to a position located on the trocar at a required position thereon;

the annular abutment collar being adjustable longitudinally along the outer surface of the trocar so as to be located at a selected position;

a clamp for clamping the annular abutment collar on the outer surface of the trocar at the selected position;

said annular expandable member being arranged while in said collapsed condition to be inserted through an incision in the body wall and expanded when inserted to engage an inside surface of the body wall;

a coupling arrangement for holding the annular expandable member attached to the annular abutment collar to form a common collar portion for common engagement onto the outer surface of the trocar;

the coupling arrangement being releasable so that when released the annular abutment collar is movable along the outer surface of the trocar longitudinally relative to and independently of the annular expandable member such that the annular abutment collar is moved to a position where the annular abutment collar is attached to the outer surface of the trocar to hold the body wall between the annular abutment collar and said annular expandable member;

and an operable device for causing said expansion movement of the annular expandable member;

said operable device being at least partly mounted on said annular abutment collar so as to be carried thereby for movement therewith longitudinally of the outer surface of the trocar;

said operable device including a connector member communicating operation of said operable device from said annular abutment collar to the annular expandable member;

said connector member being extendible and retractable between the annular expandable member and the annular abutment collar to accommodate said relative movement.

2. The trocar support apparatus according to claim 1 wherein the annular expandable member is inflatable by a fluid and the operable device comprises a container providing a source of the fluid.

3. The trocar support apparatus according to claim 2 wherein the operable device comprises a container having a fixed volume and wherein operation of said operable device causes the operable device to move from an initial position to an expelled position for supply of said fixed volume only allowing inflation of the annular expandable member only to a fixed size.

4. The trocar support apparatus according to claim 3 wherein the operable device includes a latch arranged to hold the operable device in the expelled position when the fixed volume is supplied, wherein said latch is arranged to be releasable and wherein there is provided a spring engaging the operable device and operable to return the operable device from the expelled position to said initial position to extract said fixed volume of the fluid from the annular expandable member back to the container.

5. The trocar support apparatus according to claim 2 wherein the connector member comprises a tubular conduit which connects the fluid from the operable device to said annular expandable member.

6. The trocar support apparatus according to claim 5 wherein the tubular conduit is wrapped helically in a plurality of turns around the trocar and wherein the tubular conduit is extendible and retractable by increasing and decreasing a space between the turns.

7. The trocar support apparatus according to claim 1 wherein the operable device is permanently and wholly mounted on the annular abutment collar as a component thereof for said adjustable movement therewith.

8. The trocar support apparatus according to claim 1 wherein said coupling arrangement comprises a support collar for said annular expandable member which is attached to the annular abutment collar and is configured so that the support collar moves therewith onto the trocar, and wherein the support collar is removable from the annular abutment collar and said annular expandable member when said annular expandable member reaches said required axial position.

9. The trocar support according to claim 8 wherein the support collar includes a manually operable release member to release the support collar from said annular expandable member.

10. The trocar support according to claim 9 wherein the support collar is molded from a plastic material so as to be rigid to protect said annular expandable member.

11. A trocar support apparatus for use with a trocar separate from the apparatus for maintaining the trocar in fixed position in a body wall of a patient while the trocar extends through the body wall of a patient, the support apparatus comprising:

an annular expandable member separate from the trocar and shaped and arranged to be received on and directly contact an outer surface of the trocar and movable along the trocar from a position separate from the trocar to a position located on the trocar, said annular expandable member being movable in an expansion movement from a collapsed condition radially outwardly of the trocar to a predetermined size;

an annular abutment collar separate from the trocar and shaped and arranged to be received on and directly contact an outer surface of the trocar and movable along the trocar from a position separate from the trocar to a position located on the trocar at a required position thereon;

the annular abutment collar being arranged for adjustable movement longitudinally of the trocar and relative to the annular expandable member so as to be located at a selected position to hold the body wall between the annular abutment collar and said annular expandable member;

a clamp for locating the annular abutment collar on the trocar at the selected position;

said annular expandable member being arranged while in said collapsed condition to be inserted through an incision in the body wall and expanded when inserted to engage an inside surface of the body wall;

and a manually operable device for causing said expansion movement of the annular expandable member;

said manually operable device being permanently and wholly mounted on the annular abutment collar as a component thereof for said adjustable movement therewith.

12. The trocar support apparatus according to claim 11 wherein the annular expandable member is inflatable by a fluid and the manually operable device comprises a container providing a source of the fluid.

13. The trocar support apparatus according to claim 12 wherein the container has a fixed volume and wherein manual operation of said manually operable device causes the manually operable device to move from an initial position to an expelled position for supply of said fixed volume only allowing inflation of the annular expandable member only to a fixed size.

14. The trocar support apparatus according to claim 13 wherein the manually operable device includes a latch arranged to hold the manually operable device in the expelled position when the fixed volume is supplied, wherein said latch is releasable and wherein there is provided a spring engaging the manually operable device and operable to return the manually operable device from the expelled position to said initial position to extract said fixed volume of the fluid from the annular expandable member back to the container.

15. A trocar support apparatus for use with a trocar separate from the apparatus for maintaining the trocar in fixed position in a body wall of a patient while the trocar extends through the body wall of a patient, the support apparatus comprising:
an annular expandable member separate from the trocar and shaped and arranged to be received on and directly contact an outer surface of the trocar and movable along the trocar from a position separate from the trocar to a position located on the trocar, said annular expandable member being movable in an expansion movement from a collapsed condition radially outwardly of the trocar to a predetermined size;
an annular abutment collar separate from the trocar and shaped and arranged to be received on and directly contact an outer surface of the trocar and movable along the trocar from a position separate from the trocar to a position located on the trocar at a required position thereon;
the annular abutment collar being arranged for adjustable movement longitudinally of the trocar and relative to the annular expandable member so as to be located at a selected position to hold the body wall between the annular abutment collar and said annular expandable member;
a clamp for locating the annular abutment collar on the trocar at the selected position;
said annular expandable member being arranged while in said collapsed condition to be inserted through an incision in the body wall and expanded when inserted to engage an inside surface of the body wall;
and a manually operable device movable between an initial position and an operated position for causing said expansion movement of the annular expandable member to said predetermined size which is fixed by the manually operable device;
wherein the manually operable device includes a latch arranged to hold the manually operable device in the operated position;
wherein said latch is releasable;
and wherein there is provided a spring engaging the manually operable device and operable to return the manually operable device from the operated position to said initial position to return the annular expandable member to the collapsed condition.

16. The trocar support apparatus according to claim 15 wherein the annular expandable member is inflatable by a fluid and the manually operable device comprises a container providing a fixed volume of the fluid.

17. The trocar support apparatus according to claim 15 wherein said manually operable device includes a connector member communicating from said manually operable device on the annular abutment collar to the annular expandable member, said connector member being extendible and retractable between the annular expandable member and the annular abutment collar to accommodate said relative movement.

18. The trocar support apparatus according to claim 17 wherein the annular expandable member is inflatable by a fluid and the manually operable device comprises a container providing a fixed volume of the fluid and wherein the connector member comprises a tubular conduit which connects the fluid from the operable device to said annular expandable member.

19. The trocar support apparatus according to claim 18 wherein the tubular conduit is wrapped helically in a plurality of turns around the trocar and wherein the tubular conduit is extendible and retractable by increasing and decreasing a space between the turns.

20. The trocar support apparatus according to claim 15 wherein the manually operable device is permanently and wholly mounted on the annular abutment collar as a component thereof for said adjustable movement therewith.

21. The trocar support apparatus according to claim 15 wherein there is provided a coupling arrangement for holding the annular expandable member attached to the annular abutment collar to form a common collar portion for common engagement onto the outer surface of the trocar, the coupling arrangement being releasable so that when released the annular abutment collar is movable along the outer surface of the trocar longitudinally relative to and independently of the annular expandable member.

* * * * *